US00PP22594P2

(12) United States Plant Patent
Kako et al.

(10) Patent No.: US PP22,594 P2
(45) Date of Patent: Mar. 20, 2012

(54) ***CATHARANTHUS* PLANT NAMED 'SUNNICHIROIN'**

(50) Latin Name: *Catharanthus roseus*
Varietal Denomination: Sunnichiroin

(75) Inventors: Tetsuya Kako, Shiga (JP); Kiyoshi Miyazaki, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 12/931,167

(22) Filed: Jan. 26, 2011

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — Kent L Bell
(74) *Attorney, Agent, or Firm* — C. A. Whealy

(57) ABSTRACT

A new and distinct cultivar of *Catharanthus* plant named 'Sunnichiroin', characterized by its trailing plant habit; vigorous growth habit; freely basal branching habit; freely flowering habit; long flowering period; large red purple-colored flowers; and good garden performance.

1 Drawing Sheet

Botanical designation: *Catharanthus roseus.*
Cultivar denomination: 'SUNNICHIROIN'.

BACKGROUND OF THE INVENTION

The present invention relates to a new and distinct *Catharanthus* plant, botanically known as *Catharanthus roseus* and hereinafter referred to by the name 'Sunnichiroin'.

The new *Catharanthus* plant is a product of a planned breeding program conducted by the Inventors in Higashiomi, Shiga, Japan. The objective of the breeding program is to develop new freely branching and flowering *Catharanthus* plants with trailing plant habit and attractive and unique flower coloration.

The new *Catharanthus* plant originated from a cross-pollination conducted by the Inventors in Higashiomi, Shiga, Japan in June, 2006 of a proprietary selection of *Catharanthus roseus* identified as code number Casp7-1, not patented, as the female, or seed, parent with a proprietary selection of *Catharanthus roseus* identified as code number 03-22-4, not patented, as the male, or pollen, parent. The new *Catharanthus* plant was discovered and selected by the Inventors as a single flowering plant from within the progeny of the stated cross-pollination in a controlled greenhouse environment in Higashiomi, Shiga, Japan in March, 2007.

Asexual reproduction of the new *Catharanthus* plant by vegetative cuttings in a controlled greenhouse environment in Higashiomi, Shiga, Japan since April, 2007, has shown that the unique features of this new *Catharanthus* plant are stable and reproduced true to type in successive generations.

SUMMARY OF THE INVENTION

Plants of the new *Catharanthus* have not been observed under all possible environmental conditions. The phenotype may vary somewhat with variations in environment such as temperature and light intensity without, however, any variance in genotype.

The following traits have been repeatedly observed and are determined to be the unique characteristics of 'Sunnichiroin'. These characteristics in combination distinguish 'Sunnichiroin' as a new and distinct *Catharanthus* plant:

1. Trailing plant habit.
2. Vigorous growth habit.
3. Freely basal branching habit.
4. Freely flowering habit.
5. Long flowering period.
6. Large red purple-colored flowers.
7. Good garden performance.

Plants of the new *Catharanthus* can be compared to plants of the female parent selection. Plants of the new *Catharanthus* differ from plants of the female parent selection in the following characteristics:

1. Plants of the new *Catharanthus* are more trailing than and not as upright as plants of the female parent selection.
2. Plants of the new *Catharanthus* have red purple-colored flowers whereas plants of the female parent selection have pink-colored flowers.

Plants of the new *Catharanthus* can be compared to plants of the male parent selection. Plants of the new *Catharanthus* differ primarily from plants of the male parent selection in flower color as plants of the male parent selection have pink-colored flowers.

Plants of the new *Catharanthus* can be compared to plants of the *Catharanthus roseus* 'Sunnichipink', disclosed in U.S. Plant Pat. No. 20,523. Plants of the new *Catharanthus* differ from plants of 'Sunnichipink' in the following characteristics:

1. Plants of the new *Catharanthus* have larger leaves than plants of 'Sunnichipink'.
2. Plants of the new *Catharanthus* have broader flower petals than plants of 'Sunnichipink'.
3. Plants of the new *Catharanthus* and 'Sunnichipink' differ slightly in flower color.

BRIEF DESCRIPTION OF THE PHOTOGRAPHS

The accompanying colored photographs illustrate the overall appearance of the new *Catharanthus* plant showing the colors as true as it is reasonably possible to obtain in colored reproductions of this type. Colors in the photographs may differ slightly from the color values cited in the detailed botanical description which accurately describe the colors of the new *Catharanthus* plant.

The photograph at the top of the sheet comprises a side perspective view of a typical flowering plant of 'Sunnichiroin' grown in a container.

The photograph at the bottom of the sheet comprises a close-up view of a typical flowering plant of 'Sunnichiroin'.

DETAILED BOTANICAL DESCRIPTION

The aforementioned photographs and following observations, measurements and values describe plants grown during the summer in 15-cm containers in an outdoor nursery in Higashiomi, Shiga, Japan and under commercial practice. During the production of the plants, day temperatures averaged 25° C. and night temperatures averaged. 15° C. Plants were four months old when the description and photographs were taken. In the following description, color references are made to The Royal Horticultural Society Colour Chart, 2007 Edition, except where general terms of ordinary dictionary significance are used.

Botanical classification: *Catharanthus roseus* 'Sunnichiroin'.

Parentage:

*Female, or seed, parent.*—Proprietary selection of *Catharanthus roseus* identified as code number Casp7-1, not patented.

*Male, or pollen, parent.*—Proprietary selection of *Catharanthus roseus* identified as code number 03-22-4, not patented.

Propagation:

*Type.*—By vegetative cuttings.

*Time to initiate roots, summer.*—About two weeks at 30° C.

*Time to initiate roots, winter.*—About three weeks at 25° C.

*Time to produce a rooted young plant, summer.*—About five weeks at 30° C.

*Time to produce a rooted young plant, winter.*—About six weeks at 25° C.

*Root description.*—Fibrous; white in color.

*Rooting habit.*—Freely branching; medium density.

Plant description:

*Plant and growth habit.*—Trailing plant habit; freely branching habit with numerous lateral branches developing per plant; vigorous growth habit.

*Plant height.*—About 12 cm.

*Plant diameter.*—About 42.5 cm.

Lateral branch description:

*Length.*—About 22.6 cm.

*Diameter.*—About 3 mm.

*Internode length.*—About 2.3 cm.

*Strength.*—Strong.

*Aspect.*—Decumbent.

*Texture.*—Smooth, glabrous.

*Color.*—Close to 145B.

Foliage description:

*Arrangement.*—Opposite, simple.

*Length.*—About 7.1 cm.

*Width.*—About 2.8 cm.

*Shape.*—Narrowly elliptic.

*Apex.*—Broadly acute.

*Base.*—Obtuse.

*Margin.*—Entire.

*Texture, upper and lower surfaces.*—Sparsely pubescent.

*Venation pattern.*—Pinnate; reticulate.

*Color.*—Developing leaves, upper surface: Close to 137C. Developing leaves, lower surface: Close to 144A. Fully expanded leaves, upper surface: Close to 137A; venation, close to 145D. Fully expanded leaves, lower surface: Close to 137C; venation, close to 145D.

*Petiole.*—Length: About 4.2 mm. Diameter: About 2.2 mm. Texture, upper and lower surfaces: Sparsely pubescent. Color, upper and lower surfaces: Close to 145D.

Flower description:

*Flower arrangement and habit.*—Single salverform flowers arising from upper leaf axils; freely flowering habit with usually about 43 flowers developing per plant; flowers face upright or outwardly.

*Fragrance.*—None detected.

*Flowering habit.*—Plants begin flowering about two to three weeks after planting; long flowering period, in the garden, plants flower continuously from the early summer to late autumn in Japan.

*Flower longevity.*—Individual flowers last about two to three days on the plant; flowers not persistent.

*Flower diameter.*—About 5.6 cm.

*Flower length (depth).*—About 3.7 cm.

*Tube length.*—About 2.8 cm.

*Tube diameter, at the base.*—About 1.8 mm.

*Flower bud.*—Shape: Cylindrical. Length: About 4.2 cm. Diameter: About 3.5 mm. Color: Close to 185D.

*Corolla.*—Arrangement: Five petals fused at the base and flaring outwardly forming a star-shaped flower. Petal length from throat: About 2.8 cm. Petal width: About 2.4 cm. Petal shape: Obovate. Petal apex: Cuspidate. Petal margin: Entire; slightly undulate. Petal texture, upper and lower surfaces: Smooth, glabrous; velvety. Throat texture: Smooth, glabrous. Tube texture: Sparsely pubescent. Color: Petal, when opening, upper surface: Close to N57B to N57A; towards the base, close to N74D. Petal, when opening, lower surface: Close to N155B; towards the margins, close to 55B. Petal, fully opened, upper surface: Close to 58B; stripes, close to 75C; center, close to 155B; color becoming closer to 58C with development. Petal, fully opened, lower surface: Close to N155B; towards the margins, close to 55B. Throat: Close to 145C. Tube: Close to 145C overlain with close to 178B.

*Calyx.*—Arrangement: Star-shaped calyx with five sepals fused at the base per flower. Sepal length: About 3 mm. Sepal width: About 0.9 mm. Sepal shape: Lanceolate. Sepal apex: Acute. Sepal margin: Entire. Sepal texture, upper and lower surfaces: Sparsely pubescent. Color, immature and mature, upper surface: Close to 143A. Color, immature and mature, lower surface: Close to 143A.

*Peduncles.*—Length: About 4 mm. Diameter: About 2 mm. Angle: Upright to outward. Strength: Strong. Texture: Smooth, glabrous. Color: Close to 144A.

*Reproductive organs.*—Stamens: Quantity/arrangement: Five per flower. Stamen length: About 2.6 mm. Anther shape: Narrowly elliptic. Anther size: About 2.8 mm by 1 mm. Anther color: Close to 2C. Pollen amount: Moderate. Pollen color: Close to 12D. Pistils: Quantity: One per flower. Pistil length: About 2.6 cm. Style color: Close to 145C. Stigma shape: Transversely ellipsoidal. Stigma color: Close to 145A.

Ovary color: Close to 144C. Seed/fruit: Seed and fruit development have not been observed on plants of the new *Catharanthus*.

Garden performance: Plants of the new *Catharanthus* have been observed to have good garden performance and to tolerate wind, rain and temperatures ranging from about 5° C. to about 35° C. to 40° C.

Pathogen/pest resistance: Plants of the new *Catharanthus* have not been observed to be resistant to pathogens and pests common to *Catharanthus*.

It is claimed:

1. A new and distinct *Catharanthus* plant named 'Sunichiroin' as illustrated and described.

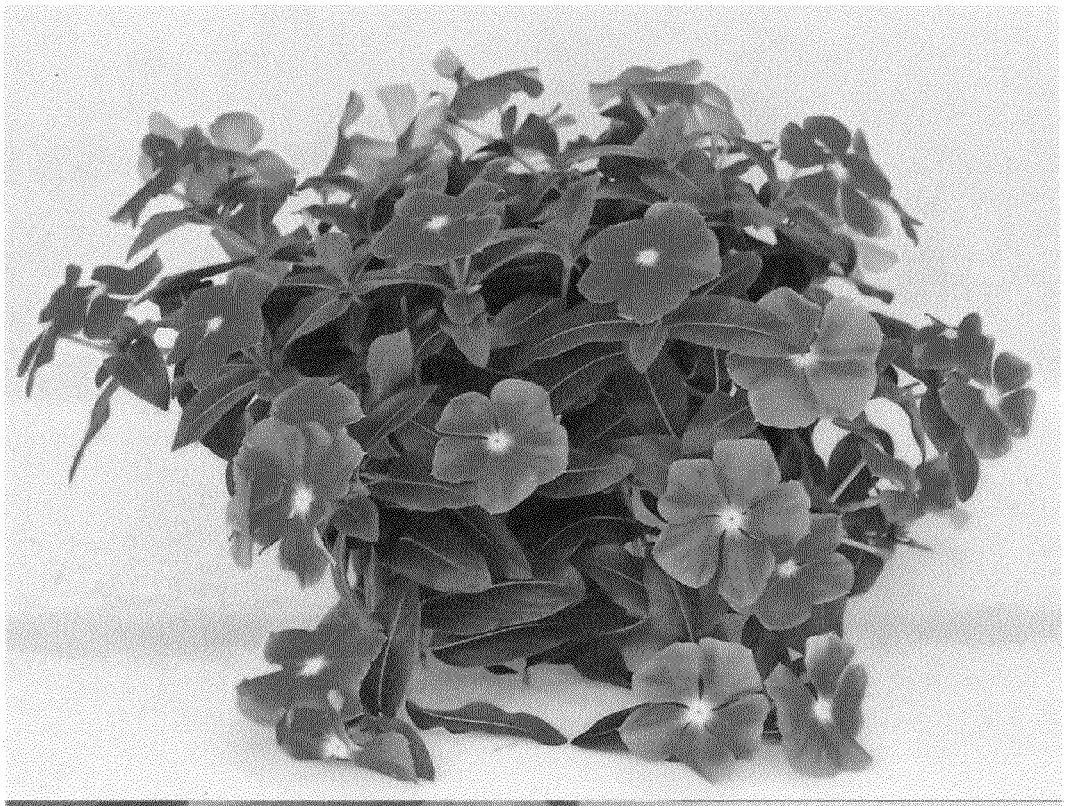
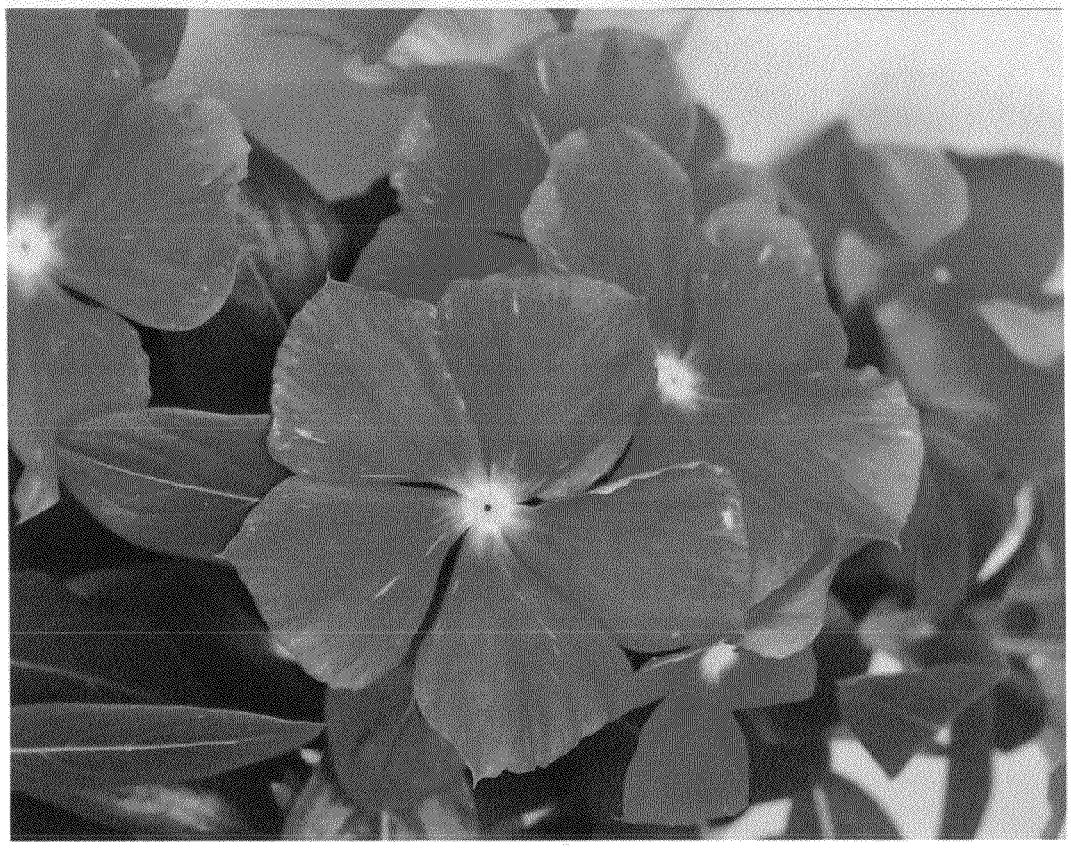

* * * * *